United States Patent
Goldberg et al.

(10) Patent No.: US 10,478,332 B2
(45) Date of Patent: Nov. 19, 2019

(54) MAGNETIC OPERATING MICROSCOPES AND METHODS OF TREATMENT AND DIAGNOSIS USING THE SAME

(71) Applicant: EMMETROPE OPHTHALMICS LLC, Key Biscayne, FL (US)

(72) Inventors: Jeffrey L. Goldberg, San Diego, CA (US); Roger A. Goldberg, Boston, MA (US)

(73) Assignee: EMMETROPE OPHTHALMICS LLC., Key Biscyane, FL (US)

( * ) Notice: Subject to any disclaimer, the term of this patent is extended or adjusted under 35 U.S.C. 154(b) by 1132 days.

(21) Appl. No.: 14/766,735

(22) PCT Filed: Feb. 6, 2014

(86) PCT No.: PCT/US2014/014984
§ 371 (c)(1),
(2) Date: Aug. 7, 2015

(87) PCT Pub. No.: WO2014/124073
PCT Pub. Date: Aug. 14, 2014

(65) Prior Publication Data
US 2016/0022485 A1  Jan. 28, 2016

Related U.S. Application Data

(60) Provisional application No. 61/762,169, filed on Feb. 7, 2013.

(51) Int. Cl.
*A61F 9/00* (2006.01)
*A61B 5/00* (2006.01)
(Continued)

(52) U.S. Cl.
CPC ............ *A61F 9/0017* (2013.01); *A61B 3/132* (2013.01); *A61B 5/05* (2013.01); *A61B 5/4839* (2013.01);
(Continued)

(58) Field of Classification Search
CPC .......... A61N 2/00; A61N 2/002; A61N 2/004; A61N 2/02; A61F 9/0017; A61B 3/13; A61B 3/132
See application file for complete search history.

(56) References Cited

U.S. PATENT DOCUMENTS 4,807,989 A   2/1989  Nagano et al.
6,135,118 A  10/2000  Dailey
(Continued)

OTHER PUBLICATIONS

T. Mimura et al., "Treatment of rabbit bullous keratopathy with precursors derived from cultured human corneal endothelium", Invest Ophthalmol Vis Sci 2005; 46: 3637-44 (Abstract).

*Primary Examiner* — Carrie R Dorna

(57) ABSTRACT

In certain aspects, the present invention is directed to a device selected from (a) an operating microscope with an attached or attachable magnet and (b) a magnet that is configured for attachment to an operating microscope. In either case, the magnet is configured to allow a patient's tissue to be viewed through the operating microscope while at the same time permitting the creation of a magnetic field of sufficient magnitude and direction to move a magnetic therapeutic and/or diagnostic agent lying within the tissue to a preferred location in the tissue.

24 Claims, 6 Drawing Sheets

(51) Int. Cl.

| | | |
|---|---|---|
| *A61N 2/00* | (2006.01) | |
| *A61B 3/13* | (2006.01) | |
| *A61K 9/00* | (2006.01) | |
| *A61B 5/05* | (2006.01) | |
| *A61K 35/30* | (2015.01) | |
| *A61K 49/08* | (2006.01) | |
| *A61M 5/00* | (2006.01) | |
| *A61M 37/00* | (2006.01) | |
| *A61N 2/02* | (2006.01) | |
| *A61N 2/06* | (2006.01) | |
| *A61B 90/20* | (2016.01) | |

(52) U.S. Cl.
CPC ............ *A61B 90/20* (2016.02); *A61K 9/0048* (2013.01); *A61K 35/30* (2013.01); *A61K 49/08* (2013.01); *A61M 5/007* (2013.01); *A61M 37/00* (2013.01); *A61N 2/002* (2013.01); *A61N 2/02* (2013.01); *A61N 2/06* (2013.01); *A61F 9/00* (2013.01); *A61K 9/0009* (2013.01); *A61K 9/0019* (2013.01); *A61M 2037/0007* (2013.01)

(56) References Cited

U.S. PATENT DOCUMENTS

| | | | |
|---|---|---|---|
| 6,402,734 B1 * | 6/2002 | Weiss ................ | A61F 9/0017 604/264 |
| 2011/0003003 A1 | 1/2011 | Goldberg et al. | |
| 2011/0060320 A1 | 3/2011 | Aharon-Attar | |
| 2012/0253102 A1 * | 10/2012 | Marban ............. | A61M 25/0068 600/12 |

* cited by examiner

MAGNETIC OPERATING MICROSCOPES AND METHODS OF TREATMENT AND DIAGNOSIS USING THE SAME

STATEMENT OF RELATED APPLICATION

This application claims the benefit of U.S. Ser. No. 61/762,169, filed Feb. 7, 2013 and entitled: "MAGNETIC OPERATING MICROSCOPES AND METHODS OF TREATMENT AND DIAGNOSIS USING THE SAME," which is hereby incorporated by reference in its entirety.

FIELD OF THE INVENTION

The present invention is related to magnets for use with operating microscopes and to methods of treatment and diagnosis using the same.

BACKGROUND

A large number of diseases and disorders result from the dysfunction of a specific tissue or organ. A number of these diseases and disorders are currently treated by transplantation, e.g., heart transplantation for certain types of cardiac dysfunction, corneal transplantation for corneal endothelial cell dysfunction, stem cells for blood cancers, and so forth. However, transplantation procedures are invasive, have varying rates of success, and are not available for many types of injuries, diseases or disorders, in particular for a number of eye diseases, for example, including certain injuries or diseases of the cornea (e.g., endothelial dystrophies, stromal dystrophies, bullous keratopathy, etc.), certain injuries or diseases of retinal ganglion cells and the optic nerve (e.g., glaucoma, retinal artery or vein occlusions, ischemic optic neuropathies, other optic neuropathies, etc.), and certain diseases of retinal photoreceptors and retinal pigment epithelium (e.g., Leber's congenital amaurosis, retinitis pigmentosa, age-related macular degeneration, etc.) For ease of reference, various parts of the eye 10 are shown in FIG. 1, specifically, the cornea 1, pupil 2, iris 3, ciliary muscle 6, lens 4, retina 5, optic nerve 7 and anterior chamber 8 (which contains the aqueous humor), and vitreous cavity 9.

Although in many cases it would seem desirable to administer new "healthy" cells, for instance, by injection or infusion, simply introducing such cells into the eye generally does not work as they do not remain localized and adhere to or become incorporated into the target tissue of a patient. For example, healthy corneal endothelial cells are inefficiently incorporated into a patient's diseased or injured cornea when injected into the anterior chamber of the eye, with the majority of cells simply falling by gravity away from the cornea, rather than properly attaching to the cornea (see, e.g., Mimura et al., *Invest. Ophthalmol. Vis. Sci.* 2005, 46(10):3637-44). Similarly, healthy retinal ganglion cells are not incorporated into the retina when injected into the vitreous cavity of the eye (see, e.g., U.S. 2011/0003003 to Goldberg et al., the disclosure of which is hereby incorporated by reference).

SUMMARY OF THE INVENTION

In certain aspects, the invention is directed to operating microscopes with associated magnets that are configured allow operator visualization of tissue while also allowing the application of a magnetic field to the tissue.

For instance, in certain embodiments, the invention provides a device selected from (a) an operating microscope with an attached or attachable magnet and (b) a magnet that is configured for attachment to an operating microscope. In either case, the magnet is configured to allow a patient's tissue to be viewed through the operating microscope while also permitting the creation of a magnetic field of sufficient magnitude and direction to move a magnetic therapeutic and/or diagnostic agent that has been introduced into the tissue to a target location in the tissue. In certain beneficial embodiments, the magnet is configured to allow the patient's tissue to be viewed through the operating microscope while simultaneously applying a magnetic field of sufficient magnitude and direction to move a magnetic therapeutic and/or diagnostic agent that has been introduced into the tissue to a target location in the tissue.

Yet other aspects of the invention pertain to kits which comprise (a) magnets with fittings for attachment to operating microscopes or operating microscopes with attached or attachable magnets and (b) one or more additional components, for example, one or more containers of a magnetic diagnostic and/or or therapeutic agent, among various other possible kit components.

Further aspects of the invention pertain to methods of treatment, which comprise (a) introducing a magnetic therapeutic and/or diagnostic agent into patient tissue and (b) providing a magnetic field of sufficient magnitude and direction to move the magnetic therapeutic and/or diagnostic agent to a target location within the tissue, while simultaneously being able to view the tissue through an operating microscope.

These and various other aspects and embodiments and as well as advantages of the present invention will become immediately apparent to those of ordinary skill in the art upon review of the Detailed Description and any appended claims to follow.

DETAILED DESCRIPTION OF THE INVENTION

Figure 1:
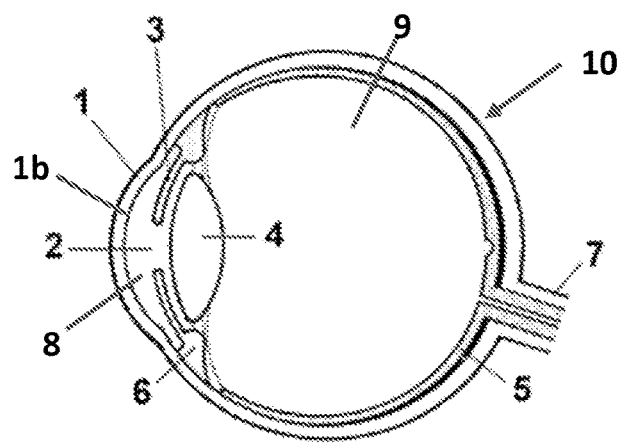
FIG. 1 is a schematic illustration of a human eye in accordance with the prior art.

A more complete understanding of the present invention is available by reference to the following detailed description of numerous aspects and embodiments of the invention. The detailed description of the invention which follows is intended to illustrate but not limit the invention.

In some aspects, the present disclosure is directed to monocular or binocular operating microscopes with associated magnets, which are adapted to allow for an operator (e.g., a surgeon, etc.) to visualize an tissue, preferably while at the same time applying a magnetic field to the tissue being viewed.

For example, during ophthalmic surgery, binocular operating microscopes may be used to enable the surgeon to have a magnified, stereoscopic view of the eye of a subject. In accordance with the present disclosure, such binocular operating microscopes may be equipped with one or more magnets which allow an operator to visualize the subject's eye while at the same time applying a magnetic field to the subject's eye. For instance, the operator may wish to use the applied magnetic field to move magnetic diagnostic and/or or therapeutic agents which are placed within the eye to a target location within the eye. In certain preferred embodiments, the center of the magnetic field of the magnet coincides with the center of the field of focus of the microscope. In certain of these embodiments, the peak centration of magnetic force induced by the magnet coincides with the center of the field of focus of the microscope, allowing maximal visualization.

Although many devices are known which can be mounted to operating microscopes (e.g., viewing systems to enable wide-field visualization of the vitreous cavity and retina, and aberrometers to measure the refractive optics of the eye, among others), the inventors are not aware of any microscope-mounted device for applying a magnetic field to the eye of a subject, including the intraocular space, while allowing visualization through the viewing system.

As used herein, "subjects" (also referred to as "patients") are vertebrate subjects, more typically mammalian subjects, including human subjects, pets and livestock.

Most materials can be classified as diamagnetic, paramagnetic, ferromagnetic or ferrimagnetic. Diamagnetic materials have a weak, negative susceptibility to magnetic fields and are thus slightly repelled by a magnetic field. Most elements in the periodic table, including copper, silver, and gold, are diamagnetic. Paramagnetic materials have a small, positive susceptibility to magnetic fields and are thus slightly attracted by a magnetic field. Paramagnetic materials include magnesium, molybdenum, lithium, and tantalum. Ferromagnetic and ferrimagnetic materials have a large, positive susceptibility to an external magnetic field and thus are strongly attracted by a magnetic field. Examples of ferromagnetic materials include iron, nickel, cobalt and some rare earth elements (e.g., gadolinium, dysprosium, etc.). Examples of ferrimagnetic materials include magnetite, maghemite and various ferrites including nickel ferrite, cobalt ferrite, manganese ferrite, nickel zinc ferrite and manganese zinc ferrite. Superparamagnetism is a form of magnetism, which appears in small ferromagnetic or ferrimagnetic nanoparticles (e.g., small particles ranging from 1-25 nm in diameter, more typically, 1-10 nm in diameter). Superparamagnetic materials are attracted by a magnetic field but relax their magnetic dipole when the field is removed, decreasing their ability to attract each other in the absence of an external magnetic field. For diagnostic and therapeutic use, this relaxation may provide certain advantages in some embodiments.

In the present disclosure, magnetic diagnostic and/or or therapeutic agents are preferably ferromagnetic or ferrimagnetic in nature, and more preferably superparamagnetic in certain applications. Specific examples of therapeutic agents include magnetic cells, for examples magnetic stem cells or magnetic ocular cells such as magnetic corneal endothelial cells and magnetic retinal pigment epithelial cells or magnetic photoreceptor cells. Further specific examples of magnetic therapeutic agents include magnetic growth factors, small molecule drugs, biological therapeutics, antibodies or antibody fragments, or cytokines. Specific examples of diagnostic agents include diagnostic agents such as magnetic fluorescent dyes, magnetic antibodies or antibody fragments, or magnetic particles that could be paired with diagnostic imaging or sensing devices such as optical coherence tomography, ultrasound, and photographic filters. Various materials can be rendered ferromagnetic or ferrimagnetic by associating them with ferromagnetic or ferrimagnetic particles such as microparticles or nanoparticles. For instance, (a) the above agents can be attached to the surface of the particles by covalent interactions and/or non-covalent interactions (e.g., interactions such as van der Waals forces, hydrophobic interactions and/or electrostatic interactions, for instance, charge-charge interactions, charge-dipole interactions, and dipole-dipole interactions, including hydrogen bonding), (b) the agents can be applied as a coating (biostable or biodegradable) that at least partially surrounds the particles, or (c) the particles can be bound to or endocytosed by the agent (e.g., a cell) and in either or both cases incorporated into the inside of the agent.

In order to generate a magnetic field having a desired magnitude and direction, the microscopes of the present disclosure are provided with one or more suitable magnets which may be selected, for example, from temporary magnets, permanent magnets and electromagnets.

Examples of permanent and temporary magnets include magnets that comprise iron, magnets that comprise neodymium, magnets that comprise cobalt, and magnets that comprise boron. Specific examples include rare earth magnets such as magnets that comprise neodymium, iron and boron (e.g., neodymium-iron-boron magnets, which commonly contain an alloy of neodymium, iron and boron, commonly in the form of a $Nd_2Fe_{14}B$ tetragonal crystalline structure), magnets that comprise samarium and cobalt (e.g., samarium-cobalt magnets, which are commonly available in two "series", specifically Series 1:5, which contain one atom of rare earth samarium for every five atoms of cobalt, and Series 2:17, which contain two atoms of rare-earth samarium and 13-17 atoms of transition metals, with the transition metal content being rich in cobalt). Specific examples further include magnets that comprise iron (e.g., ferrite magnets, which commonly have iron(III) oxide as the principle component) and magnets that comprise iron, aluminum, nickel and cobalt (e.g., Alnico magnets, which typically contain 8-12% Al, 15-26% Ni, 5-24% Co, up to 6% Cu, up to 1% Ti, and the balance Fe).

An electromagnet is a type of magnet in which a magnetic field is produced by the flow of electric current, with the strength of magnetic field generated being proportional to the amount of current. The magnetic field disappears when the current is turned off. Typically, electromagnets comprise a conductor (e.g., an insulated wire, a printed or etched conductive line, etc.) in the form of a coil. To increase the magnetic field, a coil with multiple turns may be employed. The magnetic field may be increased by positioning a ferromagnetic material (e.g., iron, etc.) inside the coil to produce a ferromagnetic-core electromagnet.

Where an electromagnet is employed in the present disclosure, a power source is also typically provided. The power source may include, for instance, a non-rechargeable battery or may include a rechargeable battery, which may be recharged, for instance, by connection to an external voltage source via a conductor (e.g., via a wire connection) or by wireless recharging (e.g., by inductive charging). The power source may also include components which control the current within the electromagnet (and thus the field strength of the electromagnet) and which control the duty cycle of the electromagnet, in other words that amount of time and frequency the electromagnet is "on" (and generating a magnetic field) and when it is "off" (and not generating a field). One advantage of the use of an electromagnet in this embodiment is the ability to titrate the field strength exerted by changing the input current to the electromagnet.

Figures 2A, 2B:
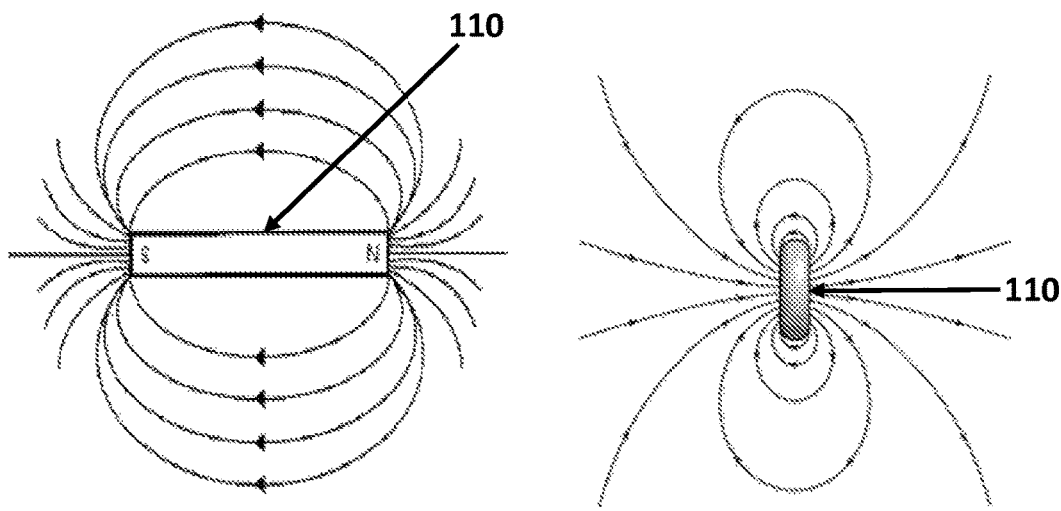
FIG. 2A is a schematic illustration of a bar magnet and associated field lines, in accordance with the prior art.
FIG. 2B is a schematic illustration of a ring-shaped magnet and associated field lines, in accordance with the prior art.

For purposes of illustration, two magnets and their associated magnetic field lines are shown schematically in FIGS. 2A and 2B.

FIG. 2A is a schematic illustration of a simple bar magnet 110 (e.g., a rare earth magnet, ferrite magnet, Alnico magnet, etc.) and the magnetic field lines associated with that magnet.

FIG. 2B is a schematic illustration of a ring-shaped magnet 110 and the magnetic field lines associated with the magnet. The ring-shaped magnet 110 may be for example, a temporary or permanent magnet (e.g., a rare earth, ferrite or Alnico magnet with poles on opposing faces of the ring) or the ring-shaped magnet 110 may be an electromagnet.

"Magnetic field lines" are lines that are drawn to show the direction of a magnetic field created by a magnet. These lines are also called "lines of force". Magnetic materials that are sufficiently mobile will migrate as a result of a magnetic field.

In various aspects, the present disclosure is directed to microscopes with associated magnets that are able to generate an intraocular magnetic field which is sufficient to physically direct a magnetic therapeutic and/or diagnostic agent (e.g., a ferromagnetic material, ferrimagnetic material, etc.) positioned inside of the eye (e.g., placed in the eye by a patient or health care provider via surface application, infusion, injection, implantation, etc.) to one or more target tissues within the eye, while at the same time allowing the eye to be view with the microscope.

For instance, in one particular embodiment, the magnet may generate a magnetic field having a magnitude and direction such that a magnetic diagnostic and/or therapeutic agent positioned in the anterior chamber of the eye is directed to the back surface of the cornea.

In another particular embodiment, the magnet may generate a magnetic field having a magnitude and direction such that a magnetic diagnostic and/or therapeutic agent positioned in the vitreous cavity of the eye is directed towards the posterior pole of the eye.

Figure 3A:
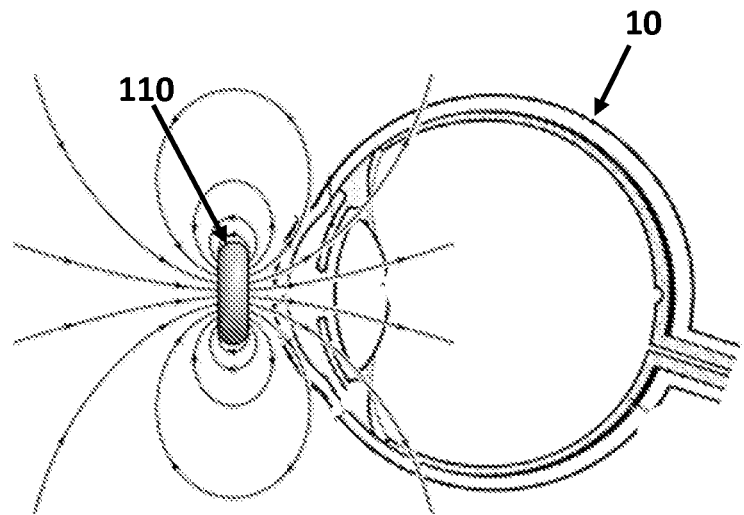
FIG. 3A is a schematic illustration of ring-shaped magnet like that of FIG. 2B in close proximity to the eye and whose magnetic field is centered with the optical axis of the eye, in accordance with an embodiment of the present invention.

FIG. 3A is a schematic illustration of a ring-shaped magnet 110 like that of FIG. 2B placed adjacent to an eye 10, the magnetic field lines associated with such a device penetrate the eye, thereby exerting a force on any magnetic material that is disposed within the eye; that force may be attractive or repulsive.

While a ring-shaped magnet like that of FIG. 2B is shown in FIG. 3A, it should be clear from the present disclosure that the invention is not limited to such a magnet. Other types of magnets may be employed so long as a magnetic field is established within the eye that is capable of directing a magnetic therapeutic and/or diagnostic agent positioned within the eye to a targeted position within the eye, while at the same time viewing the eye. In certain embodiments, a series of bar magnets may be placed in a circular pattern to generate a suitable magnetic field.

Different magnetic fields can be used to attract or repel magnetic agents to different locations within the eye. In some embodiments, a magnet positioned anterior to the eye will apply an attractive force to a magnetic material (e.g., a paramagnetic, ferromagnetic or ferrimagnetic material) within the eye in a direction that includes an anterior vector component. Consequently, magnets incorporated into microscopes in accordance with the present disclosure may be used to draw intraocular magnetized material to the anterior aspect of the eye for diagnostic or therapeutic purposes. In other embodiments, a magnet positioned anterior to the eye will apply a repulsive force to a magnetic material (e.g., a diamagnetic material) within the eye in a direction that includes a posterior vector component. Thus, a diamagnetic material may be used which is repulsed from the magnetic field, and, as in the above description, may drive the therapeutic and/or diagnostic agent to the posterior aspect of the eye.

The one or more magnets provided within the microscopes of the present disclosure typically generate a magnetic field strength, measured at the surface of the magnet, ranging from 0.01 Tesla or less to 5 Tesla or more (e.g., ranging from 0.01 Tesla to 0.025 Tesla to 0.05 Tesla to 0.1 Tesla to 0.25 Tesla to 0.5 Tesla to 1.0 Tesla to 2.5 Tesla to 5.0 Tesla). More typical magnetic field strengths may range from 0.1 to 1.0 Tesla in order to allow a force sufficient to cover the 24 mm axial length of a typical human eye. The actual field strength desired will vary depending on various factors including the distance between the magnet and the eye (e.g., the corneal apex), the depth of the target tissue within the eye, and the responsiveness or magnetic susceptibility of the therapeutic and/or diagnostic agent to the magnetic field, among other factors.

In some embodiments, the magnets of the present disclosure are configured to provide a magnetic field of constant field strength in time. In other embodiments, the magnets of the present disclosure are configured to provide a magnetic field of variable field strength as function of time. For example, it may be advantageous to be able to create a magnetic field that has an on/off duty cycle to control the extent and duration of the magnetic field, or to reverse the polarity. This may be able to help a magnetic agent placed inside the eye to circulate for extended periods of time within the eye. In another example, it may be advantageous to vibrate the magnetic agent inside the eye to generate mechanical forces or heat. In another example, it may be advantageous to titrate a magnetic field strength up or down to maximize the proposed delivery of the magnetic diagnostic and/or therapeutic device adjacent to or inside the eye.

A variety of known operating microscopes (also sometimes referred to as surgical microscopes) may be modified to create microscope-magnet assemblies in accordance with present disclosure. Operating microscopes for use in the present disclosure typically include a light source (e.g., halogen lamp,), various mechanical components which allow translation of the microscope in three dimensions, and a lens system that includes one or more objective lenses and one or more eyepieces and can provide a variety of total magnification values (e.g., ranging from 4× to 30×, among other values), a variety of field of view values (e.g., ranging from 8 mm to 70 mm, among other values) and a variety of working distances (e.g., ranging from 150 to 400 mm, among other values). Working distance is defined as the between the object being viewed and the first surface of the lens system.

Figure 4:
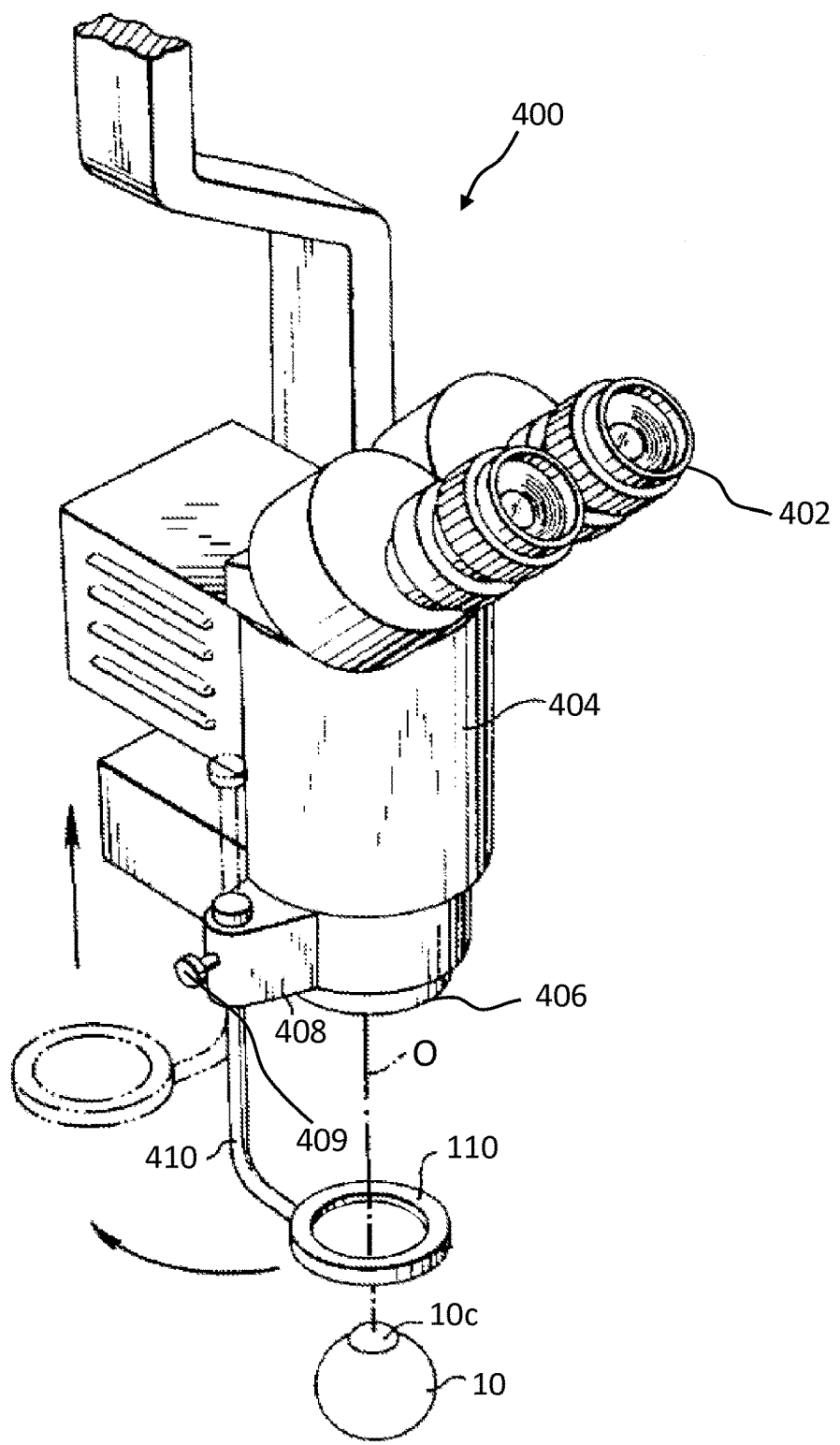
FIG. 4 is a schematic illustration of an operating microscope with an associated magnet, in accordance with an embodiment of the present invention.

FIG. 4 is a schematic illustration of a microscope-magnet assembly 400, in accordance with an embodiment of the invention. The microscope portion of the assembly includes a pair of eyepieces 402 and a microscope body 404, which contains various optical elements including an objective lens. The magnet portion of the assembly includes a magnet 110 which is shown centered with the optical axis O of the microscope. The magnet 110 is also coincident with the optical axis of the eye 10 and centered on the cornea 10c in the embodiment shown. A slide arm 410 is attached to the magnet 110. The slide arm 410 extends into a guide 408 provided on the microscope body 404. The slide arm 410 is rotatable around an axis parallel to the optical axis of the microscope and is movable up and down (i.e., in a direction of the optical axis). In the embodiment shown, the slide arm is fixed using a thumbscrew 409. One advantage of being able to move the magnet up and down (e.g., along the optical axis) is that a magnet with a lower power magnetic field may be employed to achieve a given intraocular field strength due to the ability to bring the magnet into close proximity with the eye, independent of the viewing system of the scope.

In other embodiments, the magnet 110 may be secured to the microscope body 404 on the lower surface 406 of the body 404. In some embodiments, the magnet 110 may be fixed at a position that is centered with the optical axis O of the microscope. For instance, the magnet may attached to the microscope using a standard screw-mounted system. In other embodiments the magnet 110 may be mounted on the lower surface 406 of the body 404 in a fashion that allows movement in a plane that is perpendicular to the optical axis O (e.g., by forming an assembly in which the magnet is mounted on an x-y stage, and then securing the assembly to the body). In this way, the magnetic field of the magnet may be positioned concentric with the field of view of the microscope or off-center with the field of view of the microscope. By being able to adjust the center of the magnetic field, treatment of the center of the optical axis for patients with strabismus (paralytic or restrictive), and thus an off-center optical axis, is permitted.

In other embodiments various mechanical components (which may be, for example, mechanically or electrically-driven) are provided which allow independent translation of the magnet in three dimensions (e.g., along x, y and z axes), allowing the position of the magnet to be manipulated in three dimensions relative to the optical system of the microscope. In this way, the magnet may be moved independently of both the field of view (x-y axis) and field of focus (z-axis) of the microscope. For example, the magnetic field of the magnet may be positioned concentric with the field of view of the microscope or off-center with the field of view of the microscope (e.g., concentric or off-center with the circle of light that is seen when looking into the microscope). In some embodiments, it may be beneficial to position the magnet relative to the optical system of the microscope such that the peak centration of force induced by the magnet coincides with the center of the field of focus of the microscope. Thus, the force delivered to the target tissue and its peak within the x-y plane can be manipulated without altering the field of view or depth of focus of the operating microscope.

In certain embodiments of the invention, the microscope and/or magnet may be provided with a ruler or other measuring device (e.g., an optical measuring device) to determine the distance from the magnet to the target tissue, to determine the distance from the magnet to the optical base of the microscope, or both.

In some embodiments, the magnet, as well as any associated hardware required for attachment of the magnet to the microscope, may be configured for single use (i.e., may be disposable). In other embodiments, the magnet and any associated hardware are formed from materials which allow them to be sterilized using known sterilization techniques (e.g., heat, e-beam radiation, ethylene oxide, etc.) and re-used.

The magnet 110 has an annular shape to permit viewing through the central space in the magnet while being able to applying a magnetic field. The central space may range, for example, from 10 mm to 500 mm (e.g., ranging from 10 mm to 20 mm to 30 mm to 50 mm to 100 mm to 200 mm to 300 mm to 500 mm) in width (i.e., in inner diameter), more typically ranging from 30 to 300 mm, among other values. The central space may be in the form of a hole, or it may consist of a transparent solid material such as glass or a transparent plastic (e.g., an acrylic polymer, silicone, etc.), among others. The magnet may be embedded in a sheet of transparent material.

The magnet 110 may be for example, a temporary or permanent magnet (e.g., a rare earth, ferrite or Alnico magnet with poles on opposing faces of the ring) or the magnet 110 may be an electromagnet. As noted above, where an electromagnet is employed, the power source associated with the magnet may include components which control the current within the electromagnet (and thus the field strength of the electromagnet) and which control the duty cycle of the electromagnet. One advantage of the use of an electromagnet in this embodiment is the ability to titrate the field strength exerted by the electromagnet by changing the input current to the electromagnet.

As previously indicated, in certain preferred embodiments, magnets are provided whose magnetic fields can be centered with the optical axis of the eye. Such a magnetic field may also be centered with the field of view of the scope or may be off-center with regard to the field of view of the scope In some of these embodiments (see, e.g., the schematic illustration in FIG. 4) the magnetic field directs magnetic therapeutic and/or diagnostic agents which have been positioned within the eye toward the optical axis of the eye. Because the magnet is disposed anterior to the eye, the magnetic field for such devices will be the strongest at the apex of the cornea. Consequently, magnetic therapeutic and/or diagnostic agents placed in the anterior chamber of the eye can be directed to the center of the cornea along the endothelial surface. In certain embodiments, this will help prevent the magnetic therapeutic and/or diagnostic agents from settling into the inferior anterior chamber where the cells may clog the trabecular meshwork and limit aqueous egress from the eye. Additionally, this will direct the material into the optical axis where a therapeutic and/or diagnostic effect is desired.

In other embodiments, the magnet may be configured and positioned to direct magnetic therapeutic and/or diagnostic agents which have been positioned within the eye to a point other than the than the corneal apex. For example, it may be beneficial to generate an intraocular magnetic field that is strongest at the periphery of the cornea, for example, at the iridocorneal angle (where the base of the iris attaches to the peripheral cornea and sclera), among other locations. These embodiments may be useful, for example, in treatment of glaucoma using trabecular meshwork cells, among other treatments.

Figure 3B:
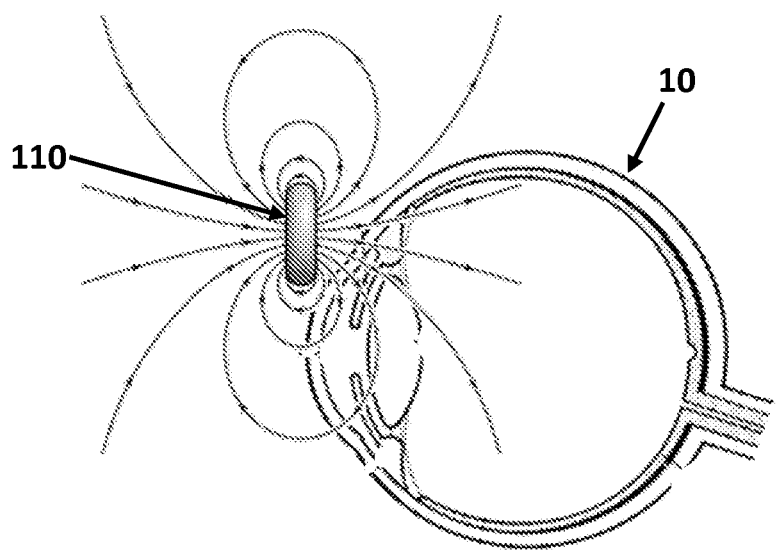
FIG. 3B is a schematic illustration of ring-shaped magnet like that of FIG. 2B in close proximity to the eye and whose magnetic field is centered on a peripheral portion of the cornea of the eye, in accordance with an embodiment of the present invention.

As one example, a magnet like that of FIG. 2B may be centered the periphery of the cornea as shown in FIG. 3B. This would direct magnetic therapeutic and/or diagnostic agents which have been positioned within the eye to a single area along the periphery of the cornea.

Figure 5:
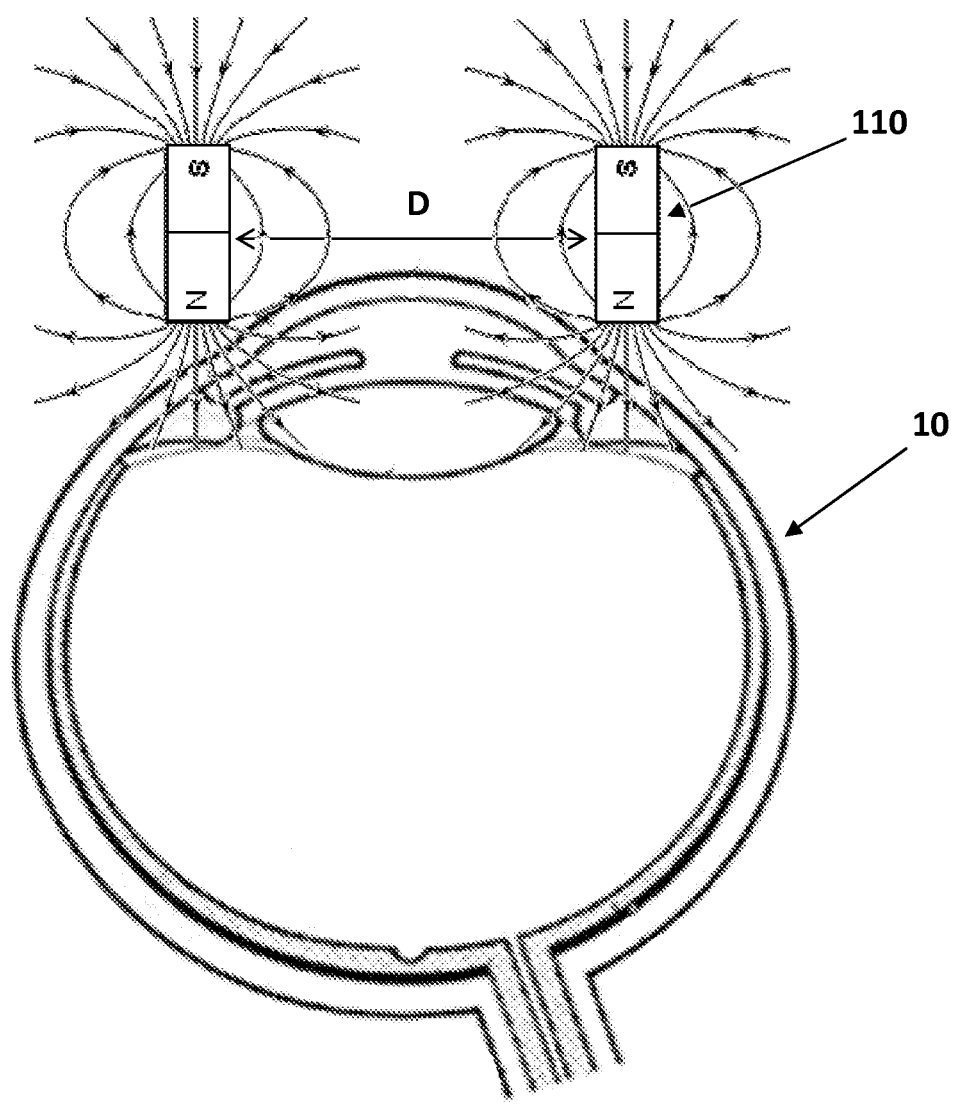
FIG. 5 is a schematic illustration of a ring-shaped magnet in which one surface represents a north pole of the magnet and an opposing surface represents a south pole of the magnet in close proximity to the eye wherein the magnetic field exhibits a maximal force over the entire periphery of the cornea, in accordance with an embodiment of the present invention.

As another example, a magnet may be employed which is centered with the regard to the cornea and which nevertheless does not generate an intraocular magnetic field that is strongest at the corneal apex. For example, a ring-shaped magnet 110 like that shown in schematic cross-section in FIG. 5 (where D is the inside diameter of the magnet) may be employed, in which one surface represents a north pole of the magnet and another opposing surface represents a south pole of the magnet. Such a magnet 110 can provide a circular region of maximum field strength whose diameter can be adjusted based on the diameter of the magnet. When centered with an optical axis of an eye 10, such a magnet 110 is capable of directing magnetic therapeutic and/or diagnostic agents which have been positioned within the eye outward from the optical axis of the eye, for example, to points around the periphery of the cornea. In still other embodiments, the center of such a magnet may be positioned off-center with regard to the optical axis of the eye.

Figure 6A:
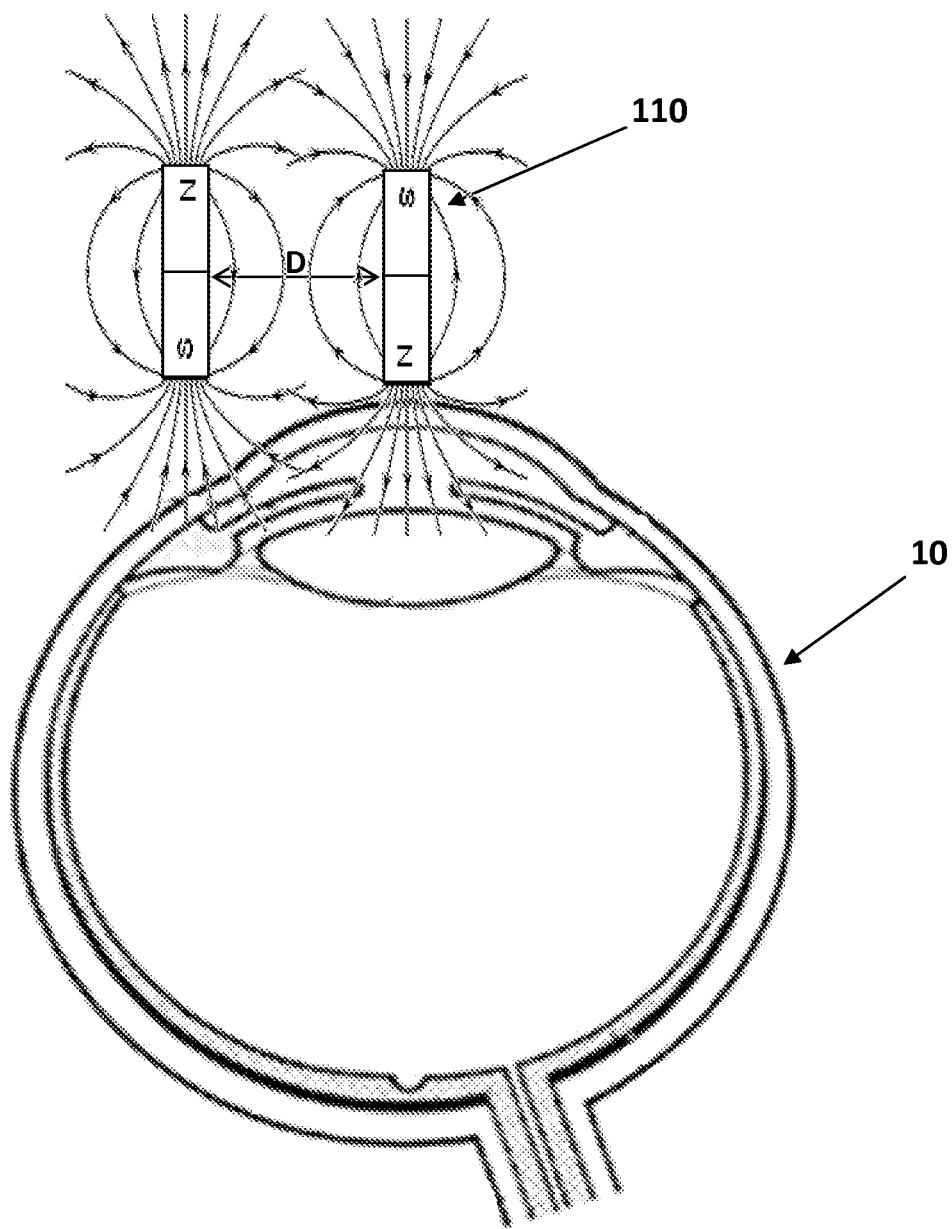
FIG. 6A is a schematic illustration of a magnet assembly in which a magnetic south pole is positioned over a peripheral portion of the cornea and a magnetic north pole is positioned over the central axis of the eye, in accordance with an embodiment of the present invention.
Figure 6B:
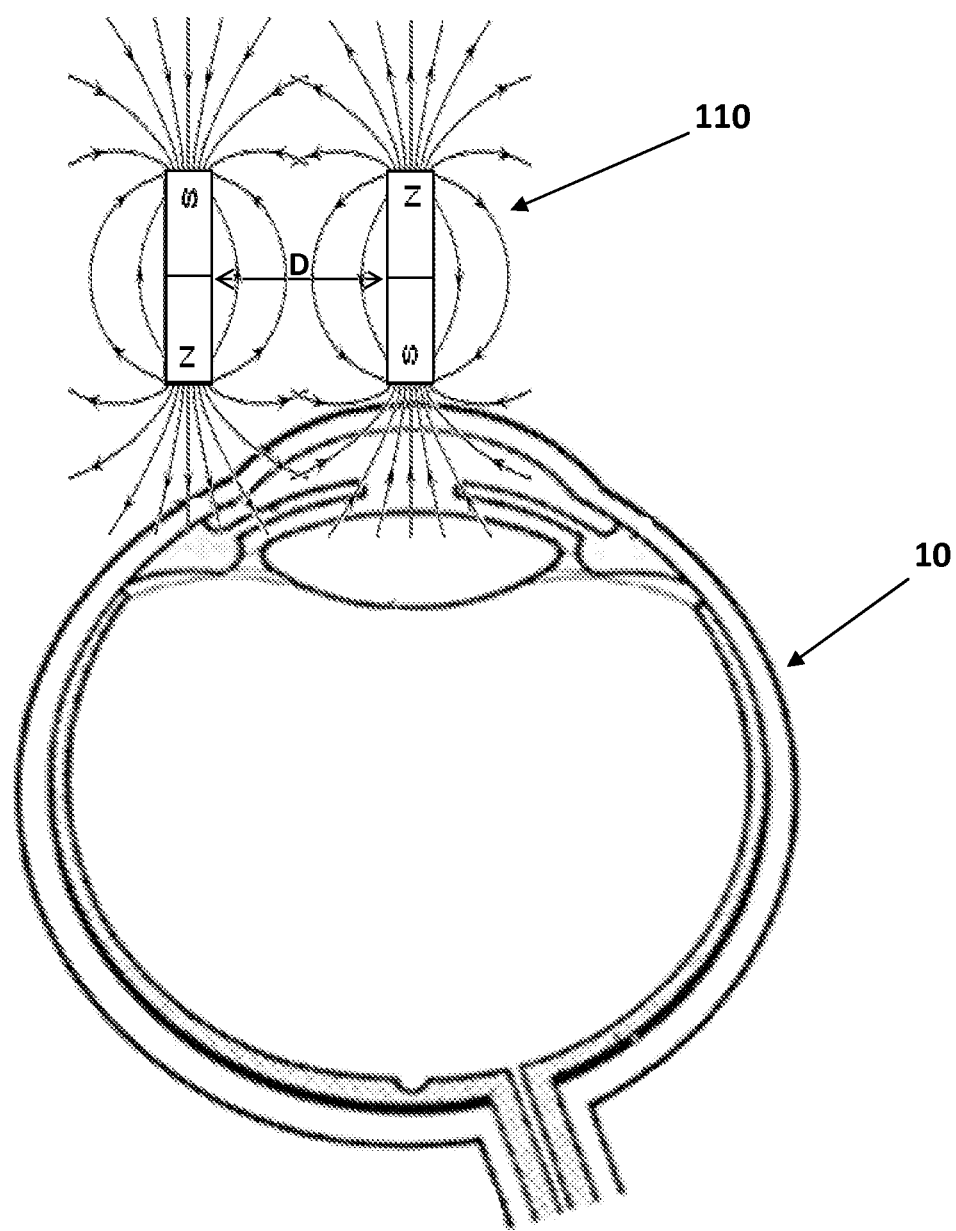
FIG. 6B is a schematic illustration of a magnet assembly in which a magnetic north pole is positioned over a peripheral portion of the cornea and a magnetic south pole is positioned over the central axis of the eye, in accordance with an embodiment of the present invention.

As another example, a magnet or multiple magnets 110 may be employed and positioned such that a magnetic south pole is positioned over a peripheral portion of the cornea and a magnetic north pole is positioned over the central axis of the eye 10 as shown in FIG. 6A. Conversely, a magnet or multiple magnets 110 may be employed and positioned such that a magnetic north pole is positioned over a peripheral portion of the cornea and a magnetic south pole is positioned over the central axis of the eye 10 as shown in FIG. 6B. These arrangements may be desirable in conjunction with certain therapeutic agents.

Further aspects of the present disclosure pertain to methods of treatment of a subject.

In a typical procedure, a magnetic therapeutic and/or diagnostic agent is introduced into the eye, for example, by injection, implantation, infusion, or surface application, among other techniques. Injection or implantation may be preferred in certain embodiments as more control is provided other than placement of the material within the eye which, in turn, assists in directing the agent to target tissue of choice. A microscope-magnet assembly as described herein can be used to both observe the eye and to apply a magnetic field to the eye, for example, beginning prior to, during or after the introduction of the magnetic therapeutic and/or diagnostic agent into the eye. In various embodiments, care is taken to ensure that the magnetic field of the device is centered on the optical axis of the eye, as previously noted.

The magnet is maintained in position for a time that is dependent upon various factors including the type of magnetic therapeutic and/or diagnostic agent employed and the length of time required to see a clinical effect, whether for therapeutic or diagnostic purposes. Typical time frames may range, for example, from 3 minutes to three hours (e.g., from 3 minutes to 5 minutes to 10 minutes to 15 minutes to 30 minutes to 1 hour to 2 hours to 3 hours), among other time frames.

In one particular embodiment, a procedure is provided in which a magnetic therapeutic and/or diagnostic agent is introduced into the anterior chamber of the eye, whereby the magnetic portion of the microscope draws those materials anteriorly to the apical aspect of the corneal endothelium. For example, magnetic corneal endothelial cells can be injected in to the anterior chamber of the eye under microscopic observation and the magnetic portion of the microscope maintained in place for anywhere from 3 minutes to 180 minutes, more typically for 5 minutes to 15 minutes after injection, to stimulate migration of the injected corneal endothelial cells to the back surface of the cornea to facilitate integration and retention of these cells into the host corneal endothelium.

Still further aspects of the present disclosure pertain to kits that are useful for diagnosing or treating a patient. The kits may include all or a subset of the components useful for treating or diagnosing a patient in accordance with the present disclosure. The kits may include, for example, any combination of two or more of the following items: (a) either a magnet that is configured to be mounted to a preexisting operating microscope or an operating microscope with an attached or unattached magnet, (b) one or more containers of a magnetic diagnostic and/or or therapeutic agent, for example, in a form that is suitable for immediate administration to a patient (e.g., in a liquid form suitable for injection, infusion or surface application, in a dry form suitable for implantation, etc.) or in a form suitable for administration upon addition of another component (e.g., in a dry form that is suitable for administration upon suspension or dissolution using a suitable liquid carrier), (c) one or more containers of a suitable liquid carrier (e.g. sterile water for injection, physiological saline, phosphate buffer, phosphate buffered saline, etc.) which may be used to reconstitute a magnetic diagnostic and/or or therapeutic agent in dry form or may be used to dilute a magnetic diagnostic and/or or therapeutic agent in liquid form, (d) an injection device (e.g., a combination syringe and needle or an iontophoresis device for administering a composition comprising a magnetic diagnostic and/or or therapeutic agent to the patient's eye), (e) instructions for administering the magnetic compositions to a patient's eye and/or for using the magnet and microscope in a surgical procedure, (f) packaging and information as required by a governmental regulatory agency that regulates cell therapy products, pharmaceuticals and/or medical devices, and (g) appropriate anesthetic and antiseptic supplies. In certain embodiments, the components of the kits are provided in a single sterile package for convenient use by a health care professional.

Where the kit comprises a magnet that is not an electromagnet (e.g., a rare earth magnet, ferrite magnet, Alnico magnet, etc.) in combination with a ferromagnetic or ferromagnetic diagnostic and/or therapeutic agent, it may be desirable to provide the kit with shielding to magnetically isolate the ferromagnetic or ferromagnetic agent from the magnet. For instance, if exposed to a magnetic field of sufficient magnitude for a sufficient time, the ferromagnetic or ferromagnetic diagnostic and/or therapeutic agent may itself become magnetized, which may lead, for example to clumping of the agent. In embodiments where shielding is desired, the ferromagnetic or ferromagnetic diagnostic and/ or therapeutic agent, the magnet, or both may be enclosed within a suitable magnetic shielding material. Examples of magnetic shielding materials include various high-permeability shielding alloys such as nickel-iron alloys including permalloy (an alloy of nickel and iron) and mu-metal (an alloy of nickel, iron, copper and molybdenum or chromium), among others.

Although various embodiments are specifically illustrated and described herein, it will be appreciated that modifications and variations of the present invention are covered by the above teachings and are within the purview of any appended claims without departing from the spirit and intended scope of the invention.

The invention claimed is:

1. A device selected from an operating microscope with an attached magnet or an attachable magnet that is configured for attachment to the operating microscope, wherein the attached magnet, or the attachable magnet when attached to the operating microscope, is configured to allow a patient's tissue to be viewed through the operating microscope while at the same time permitting the creation of an intraocular magnetic field of sufficient magnitude and direction to move a magnetic therapeutic agent, a magnetic diagnostic agent, or both, that is positioned inside the tissue to a target location within the tissue.

2. The device of claim 1, wherein the magnetic field generated by the attached or attachable magnet ranges from 0.1 Tesla to 10.0 Tesla.

3. The device of claim 1, wherein the attached or attachable magnet is a rare earth magnet.

4. The device of claim 1, wherein the attached or attachable magnet is an electromagnet comprising a conductive coil and a source of electrical power in electrical communication with the conductive coil.

5. The device of claim 1, wherein the device is the operating microscope with the attached magnet and wherein a center the magnetic field of the attached magnet is centered with an optical axis of the microscope.

6. The device of claim 1, wherein the device is the operating microscope with the attached magnet and wherein the attached magnet is movable in a plane that is perpendicular to an optical axis of the microscope.

7. The device of claim 1, wherein the device is the operating microscope with the attached magnet and wherein the attached magnet is movable along an axis that is coincident with or parallel with an optical axis of the microscope.

8. The device of claim 1, wherein the device is the operating microscope with the attached magnet and wherein a peak centration of magnetic force induced by the attached magnet coincides with a center of the field of focus of the microscope.

9. The device of claim 1, wherein the attached or attachable magnet is in the shape of a ring.

10. The device of claim 1, wherein the tissue is eye tissue and wherein the attached magnet, or the attachable magnet when attached to the operating microscope, is configured to generate an intraocular magnetic field that is strongest at an apex of the cornea.

11. The device of claim 1, wherein the tissue is eye tissue and wherein the attached magnet, or the attachable magnet when attached to the operating microscope, is configured to generate an intraocular magnetic field that is strongest at a periphery of the cornea.

12. The device of claim 1, wherein the magnetic therapeutic agent, the magnetic diagnostic agent, or both, is a ferromagnetic magnetic therapeutic agent, a ferrimagnetic therapeutic agent, a ferromagnetic diagnostic agent, or a ferrimagnetic diagnostic agent.

13. The device of claim 1, wherein the operating microscope is a binocular microscope.

14. The device of claim 1, wherein the operating microscope is an ophthalmic microscope.

15. A kit comprising a device in accordance with claim 1 and a container of a magnetic diagnostic agent, a magnetic therapeutic agent, or both.

16. The kit of claim 15, further comprising an injection device comprising a needle and a syringe.

17. The kit of claim 15, wherein the magnetic therapeutic agent, the magnetic diagnostic agent, or both, is a ferromagnetic magnetic therapeutic agent, a ferrimagnetic therapeutic agent, a ferromagnetic diagnostic agent, or a ferrimagnetic diagnostic agent.

18. The kit of claim 15, wherein the tissue is eye tissue and wherein the magnetic therapeutic agent, the magnetic diagnostic agent, or both, is selected from one or more of magnetic stem cells, magnetic corneal endothelial cells, magnetic retinal pigment epithelial cells, magnetic antibodies, magnetic growth factors, or magnetic cytokines.

19. The device of claim 1, wherein the device is the operating microscope with the attached magnet.

20. A method of treatment comprising introducing a magnetic therapeutic agent, a magnetic diagnostic agent, or both, into tissue of a patient and providing a magnetic field of sufficient magnitude and direction to move the magnetic therapeutic agent, the magnetic diagnostic agent, or both, to a target location within the tissue, while the tissue is simultaneously observable through an operating microscope and wherein the magnetic field is provided by a magnet that is attached to the operating microscope.

21. The method of claim 20, wherein the magnetic therapeutic agent, the magnetic diagnostic agent, or both, is injected into an anterior chamber of an eye and wherein the magnetic therapeutic agent, the magnetic diagnostic agent, or both, is directed to apex of the cornea.

22. The method of claim 20, wherein the magnetic therapeutic agent, the magnetic diagnostic agent, or both, is injected into an anterior chamber of the eye and wherein the magnetic therapeutic agent, the magnetic diagnostic agent, or both, is directed to the periphery of the cornea.

23. The method of claim 20, wherein the tissue is eye tissue and wherein the magnetic therapeutic agent, the magnetic diagnostic agent, or both, is selected from one or more of magnetic stem cells, magnetic corneal endothelial cells, magnetic retinal pigment epithelial cells, magnetic trabecular meshwork cells, magnetic antibodies, magnetic growth factors, and magnetic cytokines.

24. The method of claim 20, wherein the magnetic therapeutic agent, the magnetic diagnostic agent, or both, is selected from magnetic drugs and biological therapeutics.

* * * * *